United States Patent
Claude et al.

(10) Patent No.: US 10,625,076 B2
(45) Date of Patent: Apr. 21, 2020

(54) SINUS TREATMENT DEVICE WITH ADAPTIVE CIRCUIT

(71) Applicant: TIVIC HEALTH SYSTEMS INC., Menlo Park, CA (US)

(72) Inventors: John Claude, Redwood City, CA (US); Christopher A. Wiklof, Everett, WA (US)

(73) Assignee: TIVIC HEALTH SYSTEMS INC., Menlo Park, CA (US)

( * ) Notice: Subject to any disclaimer, the term of this patent is extended or adjusted under 35 U.S.C. 154(b) by 0 days.

(21) Appl. No.: 16/280,295

(22) Filed: Feb. 20, 2019

(65) Prior Publication Data
US 2019/0217087 A1    Jul. 18, 2019

Related U.S. Application Data

(63) Continuation of application No. PCT/US2018/029029, filed on Apr. 24, 2018.
(Continued)

(51) Int. Cl.
| | |
|---|---|
| *A61N 1/36* | (2006.01) |
| *A61B 5/053* | (2006.01) |
| *A61N 1/04* | (2006.01) |
| *A61N 1/02* | (2006.01) |
| *A61N 1/20* | (2006.01) |
| *A61B 5/00* | (2006.01) |

(Continued)

(52) U.S. Cl.
CPC .......... *A61N 1/36031* (2017.08); *A61B 5/053* (2013.01); *A61N 1/02* (2013.01); *A61N 1/04* (2013.01); *A61N 1/0428* (2013.01); *A61N 1/0456* (2013.01); *A61N 1/0472* (2013.01); *A61N 1/205* (2013.01); *A61N 1/36* (2013.01); *A61N 1/3601* (2013.01); *A61N 1/36014* (2013.01); *A61N 1/36021* (2013.01); *A61B 5/6814* (2013.01); *A61B 5/7225* (2013.01); *A61B 18/14* (2013.01); *A61N 1/326* (2013.01); *A61N 1/3603* (2017.08)

(58) Field of Classification Search
CPC .... A61N 1/205; A61N 1/0456; A61N 1/0428; A61N 1/36014
See application file for complete search history.

(56) References Cited

U.S. PATENT DOCUMENTS

| | | | |
|---|---|---|---|
| 4,926,880 A * | 5/1990 | Claude | A61N 1/326 600/547 |
| 5,772,605 A | 6/1998 | Weijand | |

(Continued)

FOREIGN PATENT DOCUMENTS

| | | |
|---|---|---|
| JP | 2006-000567 | 1/2006 |
| KR | 20-0389849 | 7/2005 |

(Continued)

OTHER PUBLICATIONS

PCT International Search Report and Written Opinion dated Aug. 8, 2018, for PCT International Patent Application No. PCT/US2018/029029 filed Apr. 24, 2018, 16 pages.

*Primary Examiner* — Rex R Holmes
(74) *Attorney, Agent, or Firm* — Christopher A. Wiklof; Launchpad IP, Inc.

(57) ABSTRACT

A sinus treatment device and methods of operating the sinus treatment device that includes a conductive tip and at least one return electrode are disclosed.

13 Claims, 9 Drawing Sheets

Related U.S. Application Data

(60) Provisional application No. 62/491,793, filed on Apr. 28, 2017, provisional application No. 62/559,792, filed on Sep. 18, 2017, provisional application No. 62/560,120, filed on Sep. 18, 2017.

(51) Int. Cl.
*A61B 18/14* (2006.01)
*A61N 1/32* (2006.01)

(56) References Cited

U.S. PATENT DOCUMENTS

| | | |
|---|---|---|
| 6,109,268 A | 8/2000 | Thapliyal et al. |
| 8,630,714 B1 | 1/2014 | Webb |
| 8,996,137 B2 | 3/2015 | Ackermann et al. |
| 9,002,479 B1 | 4/2015 | Unarce, Jr. |
| 9,630,003 B2 | 4/2017 | Thomopson et al. |
| 10,155,108 B2 | 12/2018 | Ackermann et al. |
| 10,252,048 B2 | 4/2019 | Loudin et al. |
| 2004/0044390 A1 | 3/2004 | Szeles |
| 2007/0293918 A1 | 12/2007 | Thompson et al. |
| 2009/0030476 A1 | 1/2009 | Hargrove |
| 2011/0276107 A1 | 11/2011 | Simon et al. |
| 2013/0085551 A1* | 4/2013 | Bachinski .......... A61N 1/36014 607/59 |
| 2014/0296934 A1 | 10/2014 | Gozani et al. |

FOREIGN PATENT DOCUMENTS

| | | |
|---|---|---|
| KR | 20-0414456 | 4/2006 |
| KR | 10-1534525 | 7/2015 |
| KR | 10-20150110935 | 10/2015 |

* cited by examiner

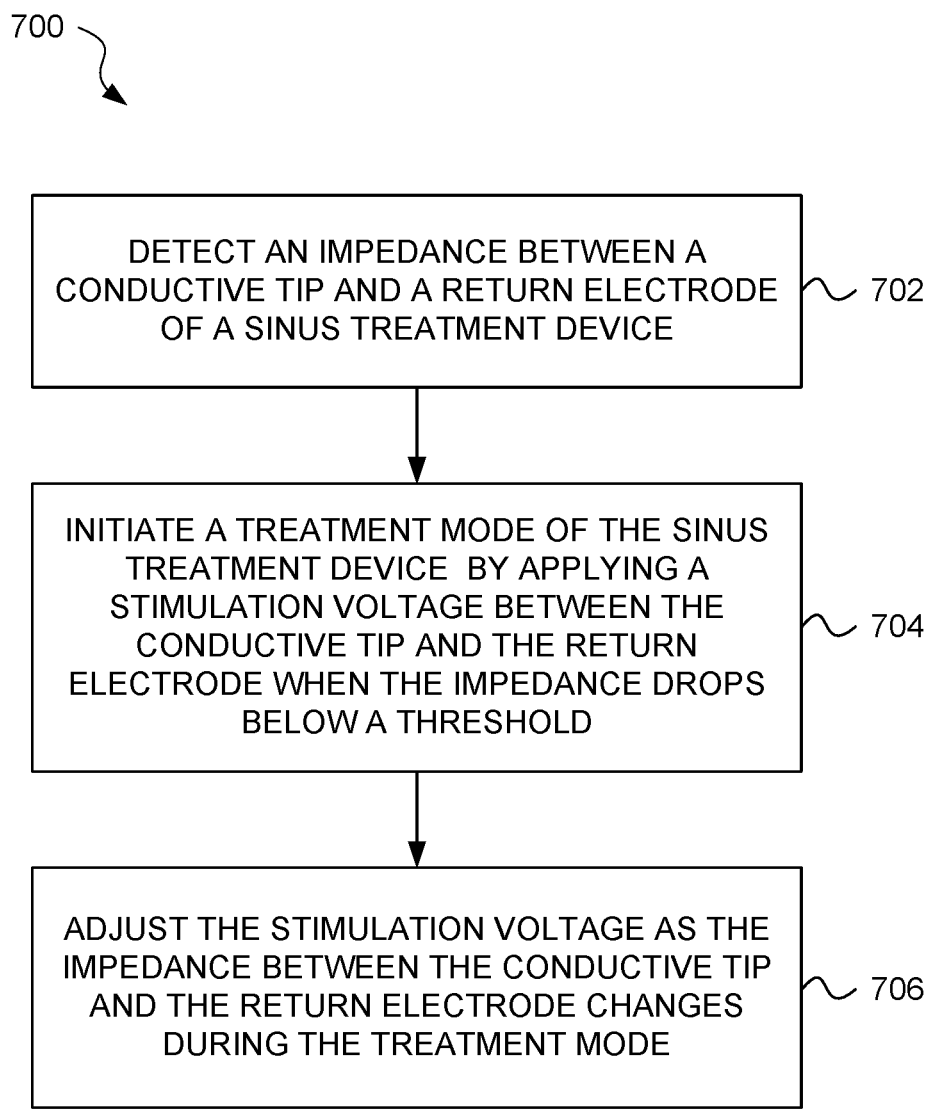

SINUS TREATMENT DEVICE WITH ADAPTIVE CIRCUIT

CROSS REFERENCE TO RELATED APPLICATIONS

The present application is a Continuation Application of International PCT Patent Application No. PCT/US2018/029029, entitled "SINUS TREATMENT DEVICE WITH ADAPTIVE CIRCUIT," filed Apr. 24, 2018. International PCT Patent Application No. PCT/US2018/029029 claims priority benefit from U.S. Provisional Patent Application No. 62/491,793, entitled "SINUS DEVICE WITH ADAPTIVE CIRCUIT," filed Apr. 28, 2017, now expired. International PCT Patent Application No. PCT/US2018/029029 also claims priority benefit from U.S. Provisional Patent Application No. 62/559,792, entitled "TREATMENT DEVICE INCLUDING WIRELESS INTERFACE AND USER APPLICATION," filed Sep. 18, 2017, now expired. International PCT Patent Application No. PCT/US2018/029029 also claims priority benefit from U.S. Provisional Patent Application No. 62/560,120, entitled "ADAPTIVE TRIGGER FOR A MICROCURRENT STIMULATION DEVICE," filed Sep. 18, 2017, now expired. Each of these applications, to the extent not inconsistent with the disclosure herein, is incorporated by reference.

BACKGROUND

Every year, millions of people suffer from sinus pain, stuffiness, and drainage associated with colds, viruses, rhinosinusitis, allergies, flus, inflammation, and infection. Sinus pain can cause symptoms consistent with headaches as nasal cavities become infected, swollen, and/or inflamed. Many sinus pain patients resort to medications that can be taken orally but which also have significant side effects including drowsiness, dry mouth, nausea, and difficulty sleeping.

What is needed is an approach that can alleviate sinus symptoms without the negative effects of conventional sinus medications.

SUMMARY

According to an embodiment, a method of operating a sinus treatment device includes detecting an impedance between a conductive tip of the sinus treatment device and a return electrode of the sinus treatment device and initiating a treatment mode of the sinus treatment device when the impedance drops below a threshold. The treatment mode also includes applying a stimulation voltage between the conductive tip and the return electrode. The method of operating the sinus treatment device also includes adjusting the stimulation voltage as the impedance between the conductive tip and the return electrode changes during the treatment mode.

According to an embodiment, a method of operating a sinus treatment device includes measuring a stimulation signal from a conductive tip of the sinus treatment device. The stimulation signal is representative of a stimulation current between the conductive tip and a return electrode attached with a body or housing of the sinus treatment device. The method of operating the sinus treatment device also includes adjusting the stimulation voltage across the conductive tip and the return electrode to keep the stimulation current at a constant value in response to measuring the stimulation signal.

According to an embodiment, a sinus treatment device includes a body or housing, conductive tip, a return electrode operatively coupled to the body of the sinus treatment device, and a stimulation driver stage coupled to apply a stimulation voltage between the conductive tip and the return electrode. The operatively coupled return electrode can include a metal adhered or plated onto a dielectric body, conductive particles embedded in the body, an inherently conductive body, and/or an aperture in the body configured to physically support a return electrode and transmit a signal to a circuit disposed in the body.

According to an embodiment, the sinus treatment device also includes a peak detector coupled to generate a peak stimulation current signal in response to receiving a stimulation signal from the conductive tip, and a microcontroller coupled to receive the peak stimulation current signal from the peak detector and coupled to the stimulation driver stage for adjusting the stimulation voltage in response to the peak stimulation current signal. The microcontroller dynamically adjusts the stimulation voltage to keep the peak stimulation current signal at a constant value.

BRIEF DESCRIPTION OF THE DRAWINGS

FIG. 7 illustrates an example flow chart illustrating an example process of operating a sinus treatment device, according to an embodiment of the disclosure.

DETAILED DESCRIPTION

Figure 1A:
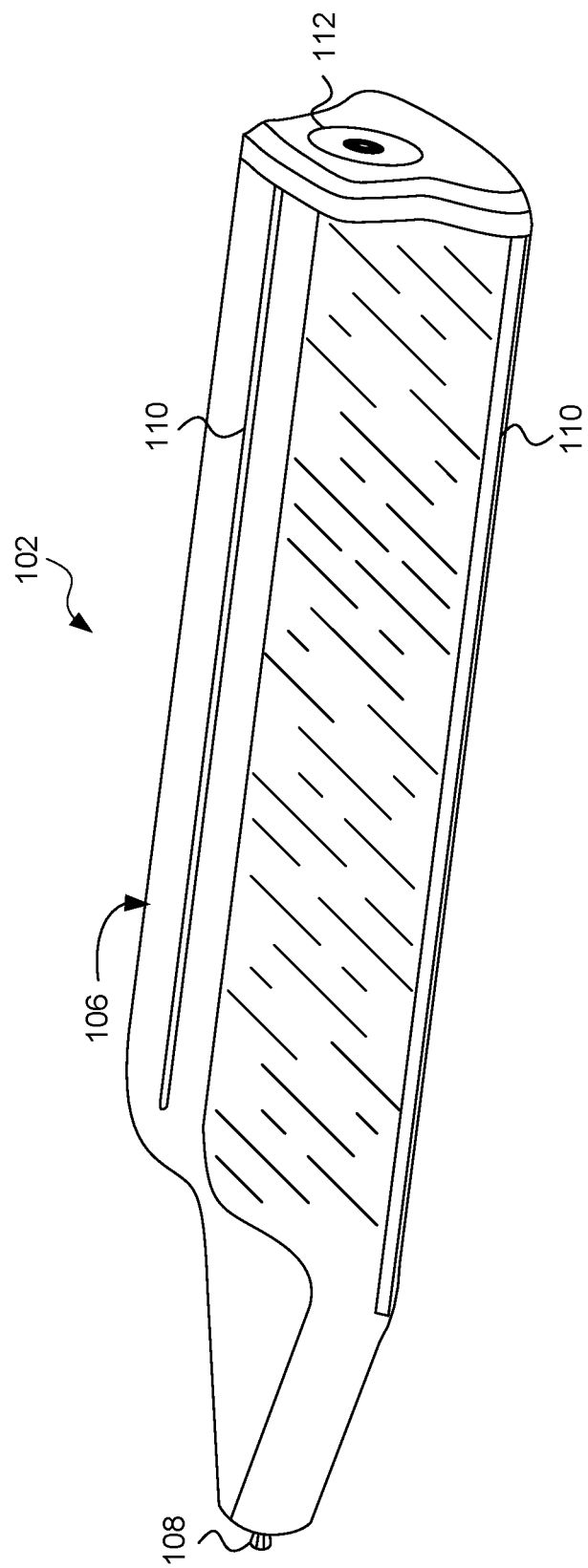
FIG. 1A is a perspective view of a sinus treatment device, according to an embodiment of the disclosure.

In the following detailed description, reference is made to the accompanying drawings, which form a part hereof. In the drawings, similar symbols typically identify similar components, unless context dictates otherwise. Other embodiments may be used and/or other changes may be made without departing from the spirit or scope of the disclosure.

FIG. 1A is a perspective view of a handheld sinus treatment device 102, according to an embodiment. The handheld sinus treatment device 102 includes a body 106, a conductive tip 108, a return electrode 110, and a charging port 112, according to an embodiment.

According to an embodiment, the handheld sinus treatment device 102 is configured to provide sinus treatment to a user. The user holds the sinus treatment device 102 in one hand, with the hand contacting the return electrode 110, places the conductive tip 108 against the skin in the sinus region (see FIG. 3) and glides the conductive tip 108 across the skin until the handheld sinus treatment device 102 detects a treatment location. When the handheld sinus treatment device 102 detects a treatment location, the handheld sinus treatment device 102 directs the user to hold the handheld sinus treatment device 102 still, and passes a stimulation current between the conductive tip 108 and the return electrode 110. The stimulation current passes through the nerve at the treatment location, thereby providing sinus relief to the user.

According to an embodiment, the body 106 is a rigid casing or housing. The body 106 has a shape that enables a user of the handheld sinus treatment device 102 to securely grip and comfortably hold the handheld sinus treatment device 102 during operation of the handheld sinus treatment device 102.

In one embodiment, the body 106 can be made from a material that is not electrically conductive. Alternatively, the body 106 can be made from a material that is electrically conductive, or can include portions that are electrically conducive, according to an embodiment. The body 106 can be made from a material that has low thermal conductivity. The body 106 is configured to protect sensitive electronic circuitry positioned within the body 106, as is described in more detail with relation to FIGS. 4-5.

According to an embodiment, the conductive tip 108 is an electrical conductor placed at a tip of the body 106. The conductive tip 108 can include a rounded shape at a point of contact with the skin of the user such that the conductive tip 108 can be placed against the skin of the user comfortably without piercing or scratching the skin. Furthermore, the shape and material of the conductive tip 108 can be selected to enable the user to comfortably glide the conductive tip 108 along the skin of the user's face adjacent to sinuses of the user. The conductive tip 108 is a treatment electrode, according to an embodiment.

According to an embodiment, the return electrode 110 includes an electrically conductive material positioned at various locations on or in the body 106. The return electrode 110 can be positioned in the body 106 at positions selected so that when the user holds the handheld sinus treatment device 102 in the user's hand, the user's hand is in contact with the return electrode 110 on one or more locations on the body 106. According to an embodiment, the return electrode 110 can include a conductive polycarbonate.

According to an embodiment, the charging port 112 is positioned at the rear of the body 106 of the handheld sinus treatment device 102. The charging port 112 is configured to receive a charging cable. When the charging cable is connected to the charging port 112, the internal battery of the handheld sinus treatment device 102 is recharged. Additionally, or alternatively, the charging port 112 can be a power supply port configured to connect to a power cable that provides power to the handheld sinus treatment device 102 while the user is using the handheld sinus treatment device 102. The charging port 112 can be a micro USB port, a USB 2.0 port, a USB 3.0 port, a USB C port, or any other kind of port that can be utilized to charge the battery of the handheld sinus treatment device 102, or to otherwise provide power to the handheld sinus treatment device 102. Additionally, or alternatively, the handheld sinus treatment device 102 can include wireless charging capability. For example, the handheld sinus treatment device 102 can include circuitry that enables inductive charging of the battery of the handheld sinus treatment device 102 such that when the handheld sinus treatment device 102 is positioned on a charging dock, the battery is recharged by inductive charging.

Figure 1B:
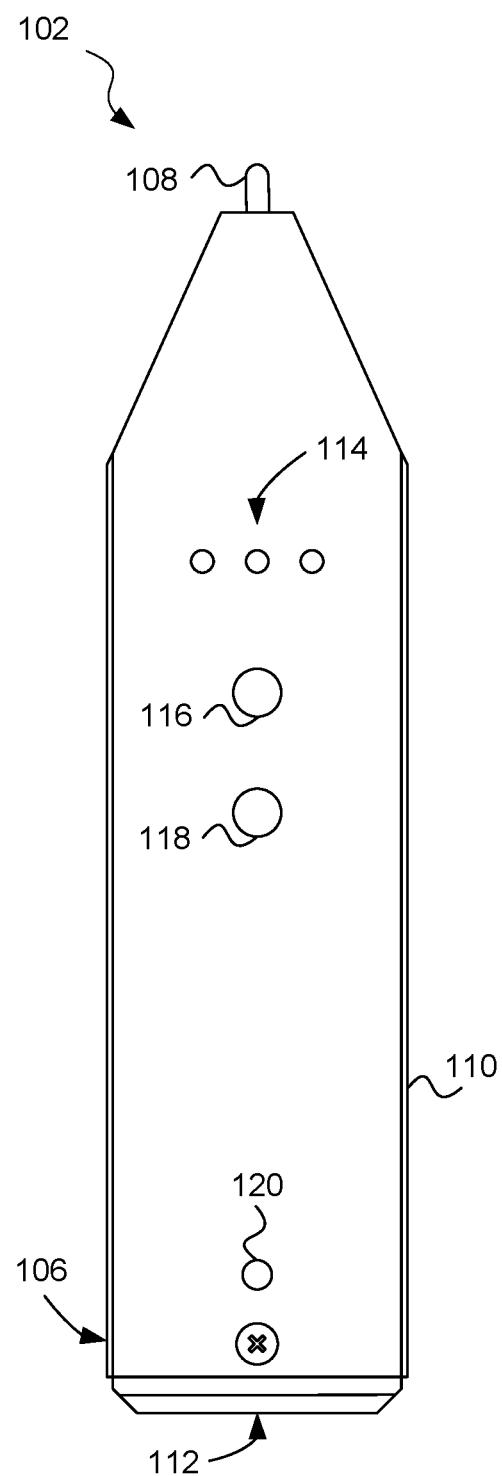
FIG. 1B is a top view of the handheld sinus treatment device of FIG. 1, according to an embodiment of the disclosure.

FIG. 1B is a top view of a handheld sinus treatment device 102, according to an embodiment. The top view of the handheld sinus treatment device 102 illustrates the body 106, the conductive tip 108, the return electrode 110, indicators 114, a sensitivity setting button 116, a power button 118, and a low battery indicator 120.

According to an embodiment, the indicators 114 can provide an indication of the sensitivity level of the handheld sinus treatment device 102. The sensitivity level corresponds to a sensitivity setting for detecting treatment areas adjacent to the sinuses of the user. The indicators 114 can include multiple LED indicators. The handheld sinus treatment device 102 can illuminate a number of the sensitivity level indicator LEDs 114 to indicate a sensitivity level of the handheld sinus treatment device 102 during a detecting mode. A greater number of illuminated indicator LEDs 114 can correspond to a higher sensitivity level. A lesser number of illuminated indicator LEDs 114 can correspond to a lower sensitivity level. Alternatively, other schemes for illuminating LEDs to indicate a sensitivity level of the detection mode of the handheld sinus treatment device 102 can be utilized. Additionally, the indicators 114 can include indicators other than LEDs. For example, the indicators 114 can include various types of lights, a display panel, or other types of indicators capable of providing an indication of the sensitivity level of the handheld sinus treatment device 102 during a detecting mode of the handheld sinus treatment device 102. According to an embodiment, the indicators 114 can also signal that a treatment location has been identified, that treatment stimulation is currently being provided, that another treatment location should be identified, or other parameters of operation of the handheld sinus treatment device 102.

According to an embodiment, the sensitivity setting button 116 is configured to enable the user to adjust the sensitivity of the handheld sinus treatment device 102 during a detecting mode. The user can manipulate the sensitivity setting button 116 in order to increase or decrease the sensitivity of the handheld sinus treatment device 102. For example, the user can press the sensitivity setting button 116 to adjust the sensitivity of the handheld sinus treatment device 102. Additionally, or alternatively, the user can toggle or slide the sensitivity setting button 116 in order to adjust the sensitivity of the handheld sinus treatment device 102. Additionally, or alternatively, the sensitivity setting button 116 can include multiple buttons for adjusting the sensitivity of the handheld sinus treatment device 102. A first button can be used to decrease the sensitivity. A second button can be used to increase the sensitivity. Additionally, or alternatively, the handheld sinus treatment device 102 can include a touchscreen that enables the user to adjust the sensitivity of the handheld sinus treatment device 102.

According to an embodiment, the power button 118 is configured to enable the user to turn the handheld sinus treatment device 102 on or off. For example, if the handheld sinus treatment device 102 is currently off, then the user can turn the handheld sinus treatment device 102 on by pressing, toggling, sliding, or otherwise manipulating, the power button 118. If the handheld sinus treatment device 102 is currently on, then the user can turn the handheld sinus treatment device 102 off by pressing, toggling, sliding, or otherwise manipulating the power button 118. Alternatively, the sensitivity setting button 116 and the power button 118 can be implemented in a single button or switch that can adjust the sensitivity or turn the handheld sinus treatment device 102 on or off based on a length of a button press, a number of button presses, or other types of manipulations of the single button.

According to an embodiment, the low battery indicator 120 can provide an indication of a state of charge of the battery of the handheld sinus treatment device 102. The low battery indicator 120 can include one or more LEDs. When the battery of the handheld sinus treatment device 102 is low, one or more LEDs of the low battery indicator 120 can become illuminated. If the low battery indicator 120 includes a single LED, then the single LED can become illuminated when the battery is nearing depletion. Conversely, the single LED may not be illuminated when the battery is not nearing depletion. Alternatively, when the battery is nearing depletion, a first LED of a first color can be illuminated to indicate that the battery is nearing depletion. If the battery is not nearing depletion, then a second LED of a second color can be illuminated indicating that the battery is not nearing depletion.

According to an embodiment, portions of the return electrode 110 are positioned on the sides of the body 106 of the handheld sinus treatment device 102. When the user grips the handheld sinus treatment device 102 such that a thumb of the user is in a position to manipulate the sensitivity setting button 116 and the power button 118, the palm and/or fingers of the hand of the user will be in contact with the portion of the return electrode 110 positioned on the sides of the body 106 of the handheld sinus treatment device 102.

Figure 1C:
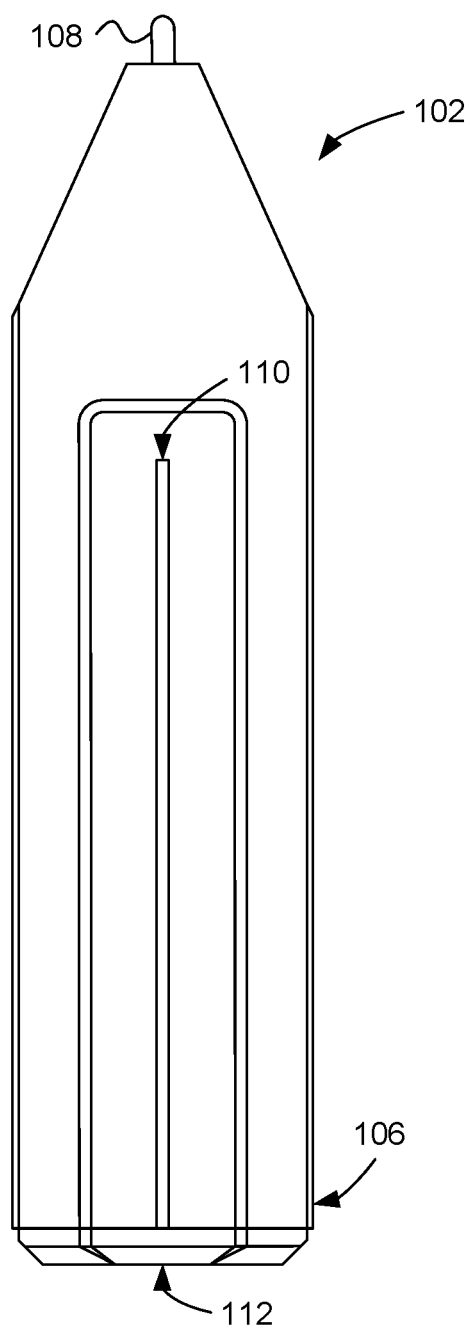
FIG. 1C is a bottom view of the handheld sinus treatment device of FIG. 1, according to an embodiment of the disclosure.

FIG. 1C is a bottom view of the handheld sinus treatment device 102 of FIG. 1B, according to an embodiment. The bottom view of the handheld sinus treatment device 102 illustrates a portion of the return electrode 110 positioned on the bottom portion of the body 106 of the handheld sinus treatment device 102. The positioning of a portion of the return electrode 110 on the bottom of the body 106 of the handheld sinus treatment device 102 further ensures that when the user holds the handheld sinus treatment device 102 in the user's hand, the user's hand will be in contact with the return electrode 110.

Figure 2:
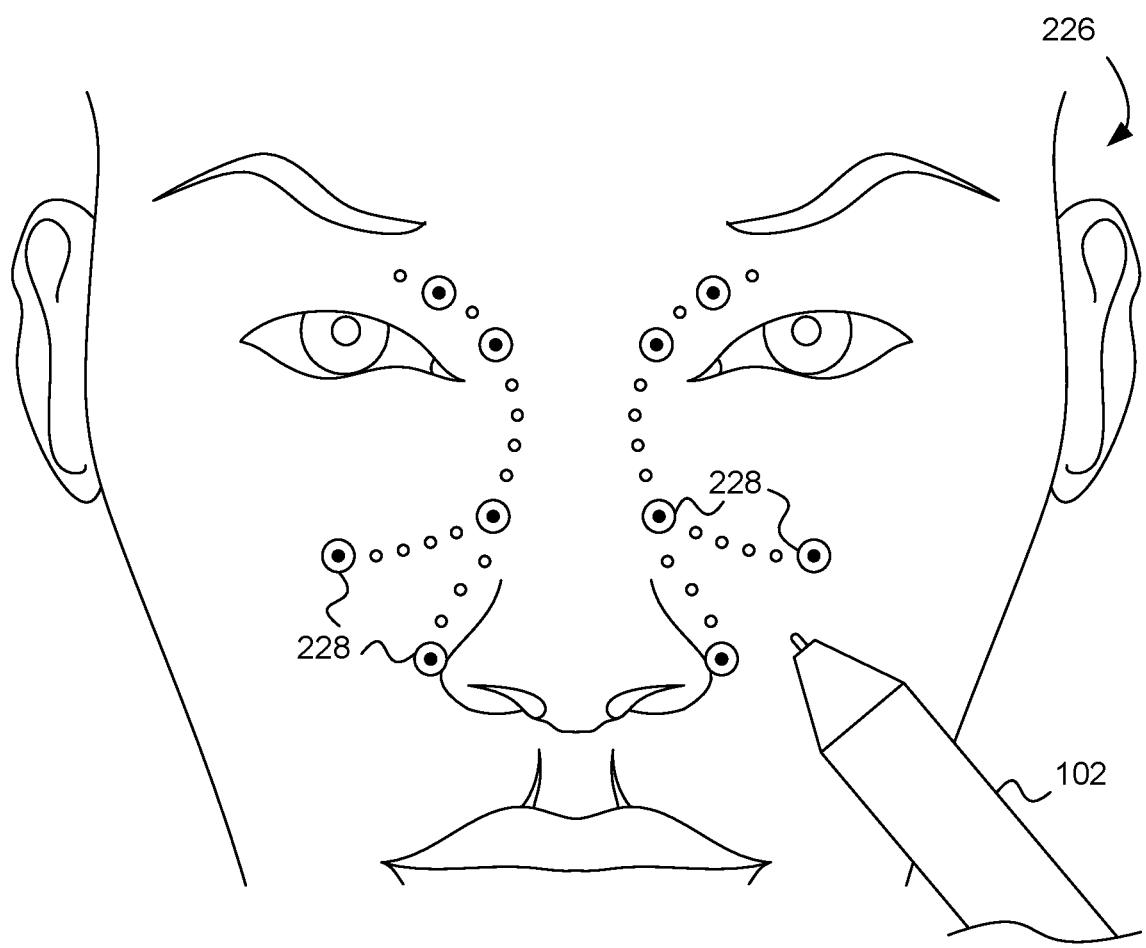
FIG. 2 is an illustration of a handheld sinus treatment device providing sinus relief treatment to highlighted treatment areas adjacent to the sinuses of a user, according to an embodiment of the disclosure.

FIG. 2 is an illustration of a face 226 of a user of the handheld sinus treatment device 102 highlighting treatment areas 228. According to an embodiment, the treatment areas 228 correspond to nerve nodes. The nerve nodes are treatment locations 228 at which sinus nerves pass through the skull.

According to an embodiment, a user uses the handheld sinus treatment device 102 by holding the body 106 in one hand such that the user's hand is in contact with portions of the return electrode 110. The user then places the conductive tip 108 on the skin adjacent to the sinuses and glides the conductive tip 108 over the skin during a detection mode of the handheld sinus treatment device 102. In the detection mode, the handheld sinus treatment device 102 detects the treatment location 228, corresponding to the location of a nerve node beneath the skin. When the handheld sinus treatment device 102 detects the treatment location 228 of a nerve node beneath the skin, the handheld sinus treatment device 102 can enter a treatment mode.

In one embodiment, the handheld sinus treatment device 102 detects treatment locations 228 by detecting an impedance between the conductive tip 108 and the return electrode 110. Treatment locations 228 are characterized by a lower impedance than surrounding areas due to enhanced conductivity of nerves.

According to an embodiment, in the treatment mode, the handheld sinus treatment device 102 provides treatment stimulation to the treatment location 228, corresponding to the nerve that is located during the detection mode. The handheld sinus treatment device 102 can provide treatment stimulation to the treatment location 228 by providing electrical stimulation to the treatment location 228. The electrical stimulation can affect the nerve node in such a way that the user experiences relief from troubling sinus symptoms such as pain, congestion, inflammation, or other unpleasant symptoms.

According to an embodiment, the handheld sinus treatment device 102 is a transcutaneous electrical nerve stimulation (TENS) device. The handheld sinus treatment device 102 applies electrical treatment stimulation in the form of a stimulation current having selected characteristics. The stimulation current can have an average magnitude that is multiple orders of magnitude lower than common TENS devices. According to an embodiment, the stimulation current does not have a DC component, but is characterized by current spikes of alternating polarity. According to an embodiment, the treatment stimulation is provided at each treatment location 228 for a period of time between 2-10 seconds.

According to an embodiment, the handheld sinus treatment device applies the stimulation current by applying a stimulation voltage between the conductive tip 108 and the return electrode 110.

According to an embodiment, the conductive tip 108 is the active electrode of a monopolar design. The housing/body 106 of the handheld sinus treatment device 102 may serve as the return electrode 110 when return electrodes 110 are integrated into the body 106. A user's hand holding the handheld sinus treatment device 102 completes the electrical path from the conductive tip 108 to the return electrode(s) 110 in that currents may travel from conductive tip 108, through the nasal area of a user and down to the hand of the user that is contacting the return electrode(s) 110, in an embodiment. These currents may be referred to as "stimulation currents" in this disclosure.

According to an embodiment, in the detection mode, the user presses the conductive tip 108 to the skin and the handheld sinus treatment device 102 initiates a low-frequency circuit that is maintained at a constant current. The handheld sinus treatment device 102 may use the current to calculate the impedance in the path between the tissue at the conductive tip 108 and the hand in contact with the handheld sinus treatment device 102. The handheld sinus treatment device 102 remains in the detection mode until the detection current indicates that the impedance is below a threshold impedance. The position of the conductive tip 108 when the impedance is below the threshold impedance corresponds to a treatment area 228. The treatment area 228 corresponds to a nerve node area. When the handheld sinus treatment device 102 identifies a treatment area 228 based on the calculated impedance, the handheld sinus treatment device 102 can enter the treatment mode and can deliver treatment stimulation to the identified treatment area 228.

According to an embodiment, the handheld sinus treatment device 102 can indicate to the user that the handheld sinus treatment device 102 is in the treatment mode and that the user should hold the conductive tip 108 at the treatment location 228 for a selected period of time. According to an embodiment, the handheld sinus treatment device 102 can indicate the transition between the detection mode and the treatment mode by the indicators 114. The indicators 114 can include one or more LEDs that can provide an illumination scheme that indicates whether the handheld sinus treatment device 102 is in the detection mode or the treatment mode.

According to an embodiment, the handheld sinus treatment device 102 can indicate that the handheld sinus treatment device 102 is in the treatment mode via haptic feedback (vibration). According to an embodiment, the handheld sinus treatment device 102 can indicate whether the handheld sinus treatment device 102 is in the detection mode, the treatment mode, or transitioning between the detection and treatment nodes by a combination of haptic feedback and LED indicators 114. According to an embodiment, when the handheld sinus treatment device 102 enters the treatment mode as indicated by one or more of LED indicators 114 and haptic feedback, the user holds the handheld sinus treatment device 102 in place until the treatment period has passed as indicated by cessation of haptic and LED indicators 114 (approximately 8 seconds in one example).

According to an embodiment, once the treatment period ends, the handheld sinus treatment device 102 resets to detection mode. The user then may continue to glide the handheld sinus treatment device 102 along the indicated path until reaching the next treatment area 228 as identified based on impedance calculations. The user may adjust the impedance sensitivity of the handheld sinus treatment device 102, in one embodiment. Changes in sensitivity adjust the impedance threshold at which the handheld sinus treatment device 102 will enter treatment mode. Changes in sensitivity do not change the output current, in one embodiment.

In one embodiment of a treatment circuit of the disclosed handheld sinus treatment device 102, the constant current stimulation output is approximately 1 Hz-1000 Hz, biphasic, no DC component signal with an average current— less than 1000 μA over a resistive load of 10K-100K Ω. The signal is presented to the patient by means of the conductive tip 108, in one embodiment. According to an embodiment, the spring-loaded conductive tip 108 activates the circuit and gently ramps the current to provide maximal comfort to user.

According to an embodiment, constant current stimulation circuit output is directed to the conductive tip 108 and returned to the circuit by way of the return electrode 110 (metallized portions of the enclosure). When the circuit is completed by the user pressing the device conductive tip 108 to the face 226, a microcontroller monitors the resulting stimulation current and controls the stimulation voltage (across the conductive tip 108 and return electrode 110) to maintain the desired current, in one embodiment. The impedance of the circuit is then calculated and monitored by the microcontroller. In the event that the impedance falls below a specified threshold, which is indicative of a treatment location, the microcontroller presents a treatment prompt through the user interface (UI), in one embodiment. According to an embodiment, the user is instructed to maintain the conductive tip 108 location until the treatment prompt has timed out. After treatment time out, the user is instructed to slowly move the conductive tip 108 to the next detected treatment location, in one embodiment.

According to an embodiment, the sensitivity level setting determines the impedance threshold at which the handheld sinus treatment device 102 will signal the user to detection of a treatment location. The treatment sensitivity threshold may be increased to compensate for higher impedance associated with dry skin or the presence of makeup, in one embodiment. Upon detection of a treatment location, the haptic motor starts to vibrate and the sensitivity level indicator LEDs 114 flash for a pre-programmed period of time, in one embodiment. If the calculated impedance increases above the threshold (conductive tip 108 removed from the face or moved to a higher impedance location on the face), the treatment session may be terminated.

In one embodiment, the handheld sinus treatment device 102 is used as a handheld microcurrent TENS device used for the temporary relief of sinus pain. The device handheld sinus treatment device 102 uses an average stimulation current that is several orders of magnitude smaller than that of previously cleared TENS devices, in one embodiment. In one embodiment, the handheld sinus treatment device 102 is a sinus treatment device designed to provide transcutaneous nerve stimulation to the regional areas associated with the sinuses, and current levels are attuned to those appropriate for facial treatments, as seen in predicate facial toners.

The sinus treatment device 102 is held in the hand, with the conductive tip 108 of the handheld sinus treatment device 102 applied to the skin on the outside of the sinus passages. In one embodiment, the conductive tip 108 is the active electrode of a monopolar design. The housing/body 106 of the handheld sinus treatment device 102 may serve as the return electrode 110 when return electrodes 110 are integrated into the body 106. A user's hand holding the sinus treatment device 102 completes the electrical path from the conductive tip 108 to the return electrode(s) 110 in that stimulation currents may travel between the conductive tip 108 and the return electrode 110 through the nasal area. The stimulation current can be passed in either direction between the conductive tip 108 and the return electrode 110 through the body of the user, according to an embodiment. The stimulation current can alternate directions during the treatment mode, according to an embodiment.

In one embodiment, when the user turns the handheld sinus treatment device 102 "ON" and presses the conductive tip 108 to the skin, the handheld sinus treatment device 102 initiates a low-frequency circuit that is maintained at a constant detection current. The handheld sinus treatment device 102 may use the detection current to calculate the impedance in the path between the tissue at the conductive tip 108 and the hand in contact with the handheld sinus treatment device 102. In one embodiment, if the calculated impedance is above an impedance threshold, the handheld sinus treatment device 102 is in "detection" mode. Conversely, in one embodiment, when the impedance falls below the impedance threshold, the handheld sinus treatment device 102 enters a "treatment" mode. In one embodiment, in the treatment mode the stimulation current is has a greater magnitude than the current used in the detection mode.

In one embodiment, the user is instructed to glide the conductive tip 108 of the handheld sinus treatment device 102 along the skin, in accordance with an embodiment of the disclosure. The switch (transition) from detection mode to the treatment mode is signaled to the user via haptic (vibration) feedback and blinking of the indicator LEDs 114, in one embodiment. The user then holds the handheld sinus treatment device 102 in place until the treatment period has passed as indicated by cessation of haptic and LED indicators 114 (approximately 8 seconds in one example), in one embodiment.

In one embodiment, once the treatment period ends, the handheld sinus treatment device 102 resets to detection mode. The user then may continue to glide the handheld sinus treatment device 102 along the indicated path until reaching the next low-impedance area. The user may adjust the impedance sensitivity of the handheld sinus treatment device 102, in one embodiment. Changes in sensitivity adjust the impedance threshold at which the handheld sinus treatment device 102 will enter treatment mode. Changes in sensitivity do not change the stimulation current, in one embodiment.

In one embodiment, the sensitivity setting button 116 may allow a user to toggle through different sensitivity levels that may be indicated by the example illustrated three indicator LEDs 114, in FIGS. 1A-1C. In one embodiment, an overcoat/insulator may cover the body 106 of the handheld sinus treatment device 102 except for where the return electrode 110 provides an electrical path.

In one embodiment, the conductive tip 108 includes an elastomeric material intended to minimize point pressure against the face 226 of the user. Various elastomers including silicone, fluorine-substituted silicones, natural rubber, vulcanized rubber, latex, latex derivatives, etc. may be used alone or in combination to form a support structure of the conductive tip 108. In another embodiment, a non-elastomeric dielectric material such as a polymer, polymer combination, or glass may be used alone or in combination to form the support structure of the active electrode. The support structure may be formed to have a relatively low thermal conductivity and/or may have a smooth radius to reduce point pressure against the skin of the user. Various conductive fibers or particles such as gold, silver, stainless steel, carbon fiber, carbon nanotubes, and/or alternating bond length (electron-conjugated) polymers are contemplated as current carriers supported by a dielectric support structure.

In one embodiment, the handheld sinus treatment device 102 includes a spring-loaded conductive tip 108 and the conductive tip 108 is a small surface area metalized feature (tip) of the enclosure that is applied to the treatment regions of the face 226. In one embodiment, a microswitch initiates the therapy circuit when the conductive tip 108 is depressed. The handheld sinus treatment device 102 may include a microprocessor microcontroller, a battery, and a transformer/voltage step-up circuit. In one embodiment, the return electrode 110 is a large surface area metalized region of the enclosure that is in contact with the user's hand.

In one embodiment, the user interface of the handheld sinus treatment device 102 includes an LED treatment indicator 114 (e.g., LEDs 114), a sensitivity level adjustment button 116, and a haptic feedback circuit. The LED sensitivity level indicates selected sensitivity levels in addition to low battery and charge status, and on/off button with integrated LED(s) to indicate "on" or "off" state, and a haptic feedback circuit.

In one embodiment, the handheld sinus treatment device 102 includes an overcoat that is electrically insulated. The overcoat may cover a portion of the metalized return electrode 110 so long as a portion (e.g., 10%) of the return electrode 110 is exposed. In one embodiment, the handheld sinus treatment device 102 includes a battery charging port 112 and circuit to charge an internal battery.

As described above, the handheld sinus treatment device 102 may be used as a TENS device that applies microamp electrical stimulation to facial nerves around the sinuses which are the regions around the nose and the supraorbital region of the eye. The locations of the low impedance points in the facial skin correlate strongly with various foramina (holes) through which major nerve fibers pass from the sinus passages, through the skull, to areas near the skin.

Figure 3B:
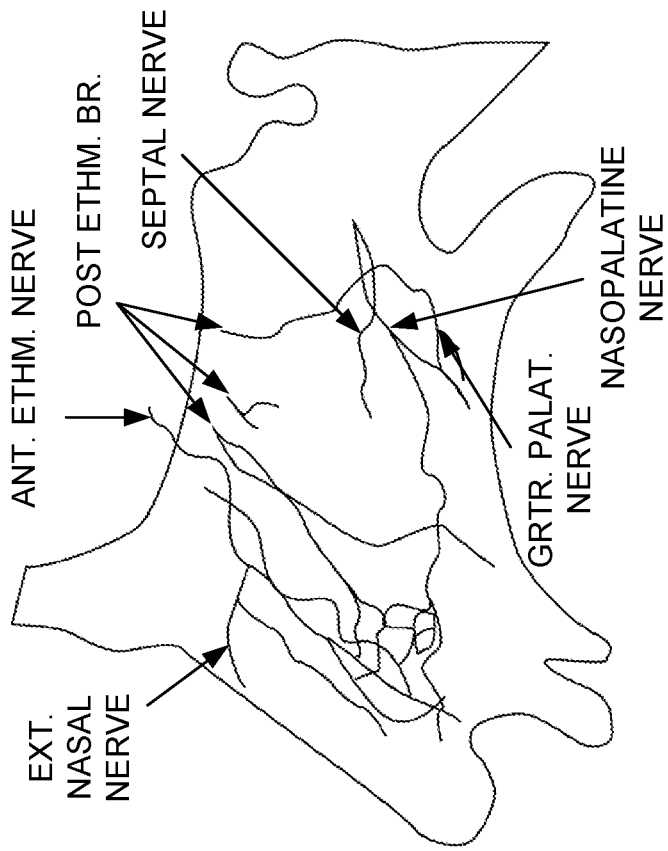
FIGS. 3A and 3B illustrate nasal pathways and associated nerves that a sinus treatment device may be applied to, according to an embodiment of the disclosure.
Figure 3A:
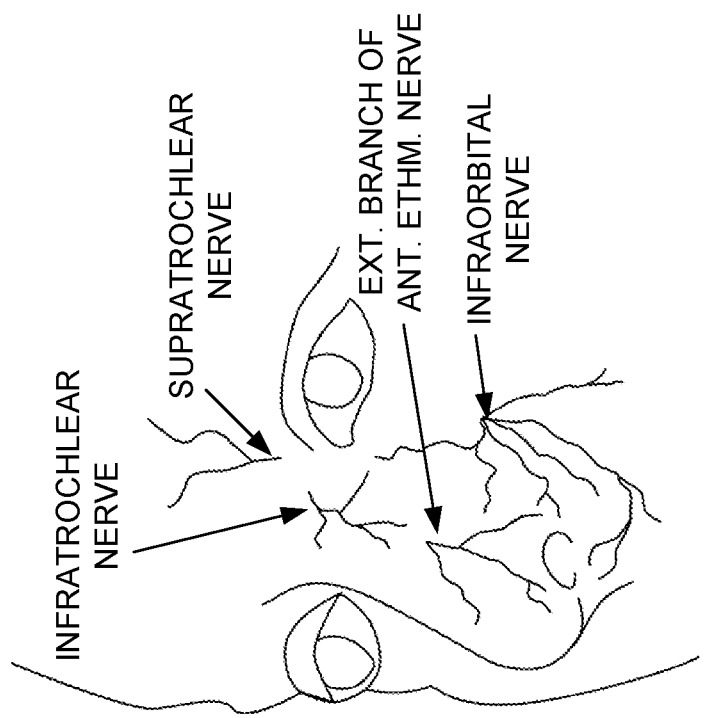

FIGS. 3A and 3B illustrate nasal pathways and associated nerves that the handheld sinus treatment device 102 may be applied to by a user to facilitate treatment/therapy.

In one embodiment of a treatment circuit of the disclosed handheld sinus treatment device 102, the constant current stimulation output is approximately 1 Hz-1000 Hz, biphasic, no DC component signal with an average current of—less than 1000 µA over a resistive load of 10K-100K Ω. The signal is presented to the patient by means of the monopolar electrode, in one embodiment. In one embodiment, the spring-loaded conductive tip 108 activates the circuit and gently ramps the current to provide maximal comfort to user.

In one embodiment, constant current stimulation circuit output is directed to the conductive tip 108 (the device tip 108) and returned to the circuit by way of the return electrode 110 (metallized portions of the enclosure). When the circuit is completed by the user pressing the device tip 108 to the face 226, a microcontroller monitors the resulting stimulation current and controls the stimulation voltage (across the conductive tip 108 and return electrode 110) to maintain the desired current, in one embodiment. The impedance of the circuit is then calculated and monitored by the microcontroller. In the event that the impedance falls below a specified threshold, which is indicative of a treatment location 228, the microcontroller presents a treatment prompt through the user interface (UI), in one embodiment. In one embodiment, the user is instructed to maintain the conductive tip 108 location until the treatment prompt has timed out. After treatment time out, the user is instructed to slowly move the conductive tip 108 to the next detected treatment location 228, in one embodiment.

In one embodiment, the sensitivity level setting determines the impedance threshold at which the handheld sinus treatment device 102 will signal the user to detection of a treatment location 228. The treatment sensitivity threshold may be increased to compensate for higher impedance associated with dry skin or the presence of makeup, in one embodiment. Upon detection of a treatment location 228, the haptic motor starts to vibrate and the sensitivity level indicator LEDs 116 flash for a pre-programmed period of time, in one embodiment. If the calculated impedance increases above the threshold (conductive tip 108 removed from the face 226 or moved to a higher impedance location on the face 226), the treatment session may be terminated.

Figure 4:
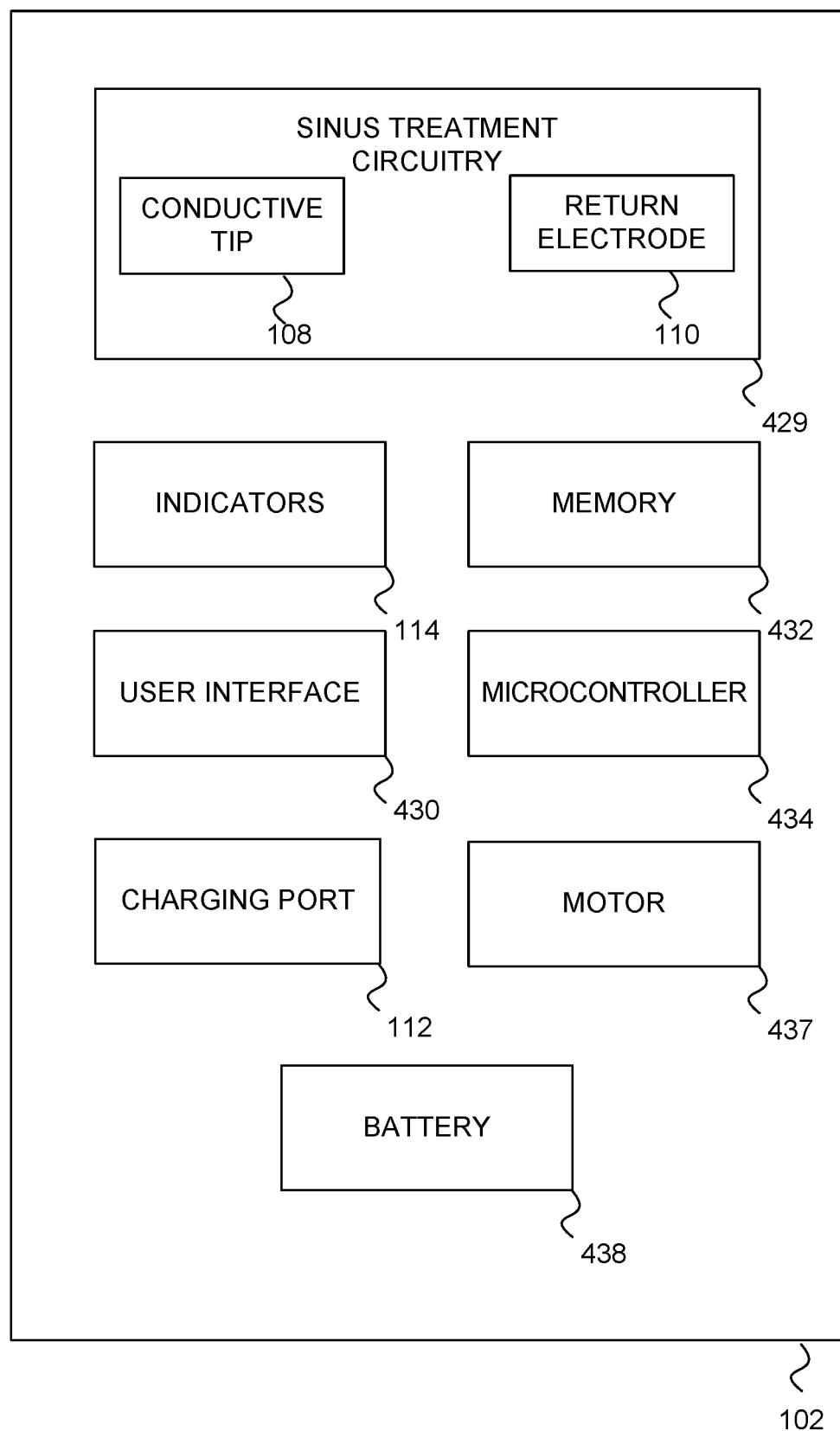
FIG. 4 is a block diagram of a sinus treatment device, according to an embodiment of the disclosure.

FIG. 4 is a block diagram of the handheld sinus treatment device 102, according to an embodiment. The handheld sinus treatment device 102 includes a sinus treatment circuitry 429, the charging port 112, indicators 114, a user interface 430, a memory 432, a microcontroller 434, a motor 437, and a battery 438. The current output circuit 429 includes the conductive tip 108 and the return electrode 110. The handheld sinus treatment device 102 utilizes these components to provide effective sinus relief treatments to the user.

According to an embodiment, the conductive tip 108 and the return electrode 110 cooperate together to provide both detection currents and treatment stimulation. Detection and treatment currents are passed between the conductive tip 108 and the return electrode 110 through the body of the user. In particular, the conductive tip 108 is positioned in contact with the user's skin to the sinus areas of the user. The return electrode 110 is in contact with the user's hand as the user holds the handheld sinus treatment device 102. The detection and treatment currents pass between the conductive tip 108 and return electrode 110 via the hand, body, and facial skin of the user.

According to an embodiment, the indicators 114 provide indications to the user as to the current mode of operation of the handheld sinus treatment device 102. Indicators 114 can include one or more LEDs that can be illuminated in selected ways to indicate whether the handheld sinus treatment device 102 is powered on, whether the handheld sinus treatment device 102 is in a treatment mode, whether the handheld sinus treatment device 102 is in a detection mode, whether the handheld sinus treatment device 102 awaits user input, whether the handheld sinus treatment device 102 is communicating with the personal electronic device 104, or indications of other types of functionality of the handheld sinus treatment device 102. According to an embodiment, the indicators 114 can include a display capable of outputting text or images to indicate to the user the various functions of the handheld sinus treatment device 102.

According to an embodiment, the user interface 430 includes various components that enable the user to control functionality of the handheld sinus treatment device 102. The user interface 430 can include the power on-off button 118, the sensitivity setting button 116, or other kinds of buttons, switches, touchscreens, or input controls that enable the user to control functionality of the handheld sinus treatment device 102. The user can manipulate the user interface 430 in order to control the functionality of the handheld sinus treatment device 102.

According to an embodiment, the memory 432 stores data related to the functionality of the handheld sinus treatment device 102. The memory 432 can include software instructions by which the various functionalities of the handheld sinus treatment device 102 can be implemented. The memory 432 can include reference impedance values and/or threshold impedance values. The reference and threshold impedance values can be utilized in the detection mode of the handheld sinus treatment device 102. The memory 432 can include data indicating previously detected treatment locations 228. The memory 432 can include other settings such as treatment lengths, treatment stimulation strengths, frequencies of treatments, or other settings including default settings and user selected settings for operation of the handheld sinus treatment device 102. The memory 432 can include one or more of EEPROMs, flash memory, ROMs, SRAM, DRAM, or other kinds of computer readable media capable of storing instructions that can be executed by the microcontroller 434.

According to an embodiment, the motor 437 enables the handheld sinus treatment device 102 to provide haptic feedback to the user. For example, during a treatment mode in which the handheld sinus treatment device 102 provides stimulation treatment to a treatment area 228, the motor 437 can cause the handheld sinus treatment device 102 to vibrate mildly to indicate to the user that the handheld sinus treatment device 102 is in the treatment mode. The motor 437 can cease the vibration to indicate that the handheld sinus treatment device 102 is no longer in the treatment mode. The motor 437 can generate vibrations to provide a variety of types of indications to the user of the handheld sinus treatment device 102.

According to an embodiment, the battery 438 provides power to the handheld sinus treatment device 102. The battery 438 can include a rechargeable battery 438 that enables the user to recharge the battery 438 after the battery 438 has become depleted through use. The battery 438 can be a lithium-ion battery, a NiCad battery, a carbon zinc battery, an alkaline battery, a nickel metal hydride battery, or other types of batteries.

According to an embodiment, the charging port 112 enables the user to recharge the battery 438. For example, the charging port 112 can be configured to receive a charging cable that connects the charging port 112 to a power source. Charging port 112 can include a micro USB port, a USB 2.0 port, a USB 3.0 port, a USB C port, or other types of charging ports. According to an embodiment, the charging port 112 enables the charging and data transmission. When a charging cable is plugged into the charging port 112, the battery 438 can be charged and data can be received or transmitted over the charging cable via the charging port 112. According to an embodiment, the handheld sinus treatment device 102 can operate while a charging cable is attached to the charging port 112. Thus, if the battery 438 is depleted, the user can attach a charging cable to the charging port 112 and can operate the handheld sinus treatment device 102 from power received via the charging port 112.

According to an embodiment, the microcontroller 434 controls the functionality of the other components of the handheld sinus treatment device 102. The microcontroller 434 is communicatively coupled to the conductive tip 108, the return electrode 110, the indicators 114, the memory 432, the user interface 430, and the charging port 112.

According to an embodiment, the microcontroller 434 executes the software instructions stored in the memory 432 to implement the various modes of functionalities of the handheld sinus treatment device 102. The microcontroller causes the conductive tip 108 and the counter electrode 110 to pass the detection currents in the detection mode, and to pass the treatment stimulation currents in the treatment mode. The microcontroller 434 controls the indicators 114 to indicate the various modes of functionalities of the handheld sinus treatment device 102. The microcontroller 434 communicates with the user interface 430 to enable the user to select various modes of operation of the handheld sinus treatment device 102.

Figure 5:
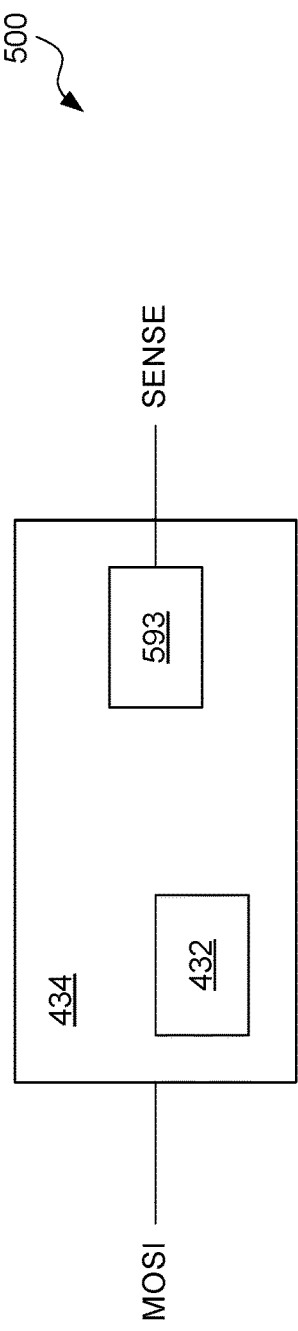
FIG. 5 illustrates an example adaptive output circuit for use with a sinus treatment device, according to an embodiment of the disclosure.
Figure 5:
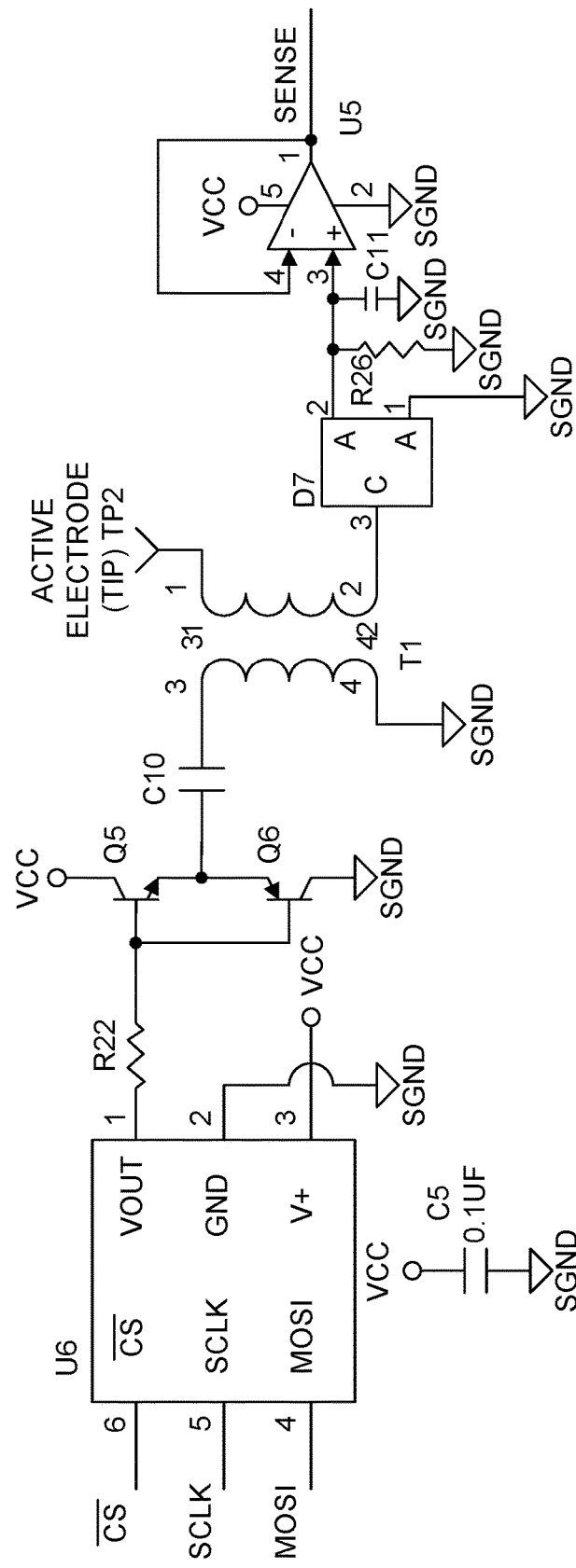

FIG. 5 illustrates an example sinus treatment circuitry 500 for use with the handheld sinus treatment device 102, according to an embodiment of the disclosure. The sinus treatment circuitry 500 is positioned within the housing/body 106, according to one embodiment. The sinus treatment circuitry 500 includes a microcontroller 434 including a memory 432 and an analog-to-digital converter (ADC) 593. In the illustrated embodiment of FIG. 5, the sinus treatment circuitry 500 also includes a stimulation driver stage and a peak detector.

In one embodiment, the stimulation driver stage is coupled to apply a stimulation voltage between the conductive tip (active electrode TP2) and the return electrode 110 (not illustrated in FIG. 5). In the illustrated embodiment, the stimulation driver stage includes a digital-to-analog converter (DAC), an amplifier, a transformer, and a capacitor. In one embodiment, the DAC (U6) is coupled to generate an analog voltage (pin 1 of U6, VOUT) in response to a digital instruction from the microcontroller 434 received via the MOSI (Master Out Slave In) communication channel of pin 4 of U6.

In the illustrated embodiment, the amplifier includes transistors Q5 and Q6 and is coupled to generate an amplified analog voltage (emitter node of Q5) in response to receiving the analog voltage from the DAC (U6).

In the illustrated embodiment, the transformer T1 includes a primary side (nodes 3 and 4) and a secondary side (nodes 1 and 2). The conductive tip (active electrode TP2) is coupled to node 1 of the secondary side of the transformer T1, in the illustrated embodiment.

In the illustrated embodiment, capacitor C10 is coupled between the amplifier and a primary side of the transformer T1 to block the DC (direct current) portions of the amplified analog signal.

In one embodiment, the peak detector includes a diode element, a buffer circuit, and a sample and hold circuit. In the illustrated embodiment, the diode element is D7. In one embodiment, the buffer circuit is coupled to output a peak stimulation current signal. In one embodiment, the peak detector is coupled to generate a peak stimulation current signal on the node 1 output of op-amp U5 in response to receiving a stimulation signal from the conductive tip. In the illustrated embodiment, the stimulation signal may travel from the conductive tip TP2 to node 2 of the transformer T1 via node 1 of the transformer T1.

In one embodiment, the sample and hold circuit is coupled between the diode element (e.g., D7) and the buffer circuit and the diode element is coupled between the secondary side of the transformer and the sample and hold circuit. In the illustrated embodiment, the sample and hold circuit includes resistors R26 and capacitor C11.

In one embodiment, the microcontroller 434 is coupled to receive the peak stimulation current signal (SENSE) from the peak detector and coupled to the stimulation driver stage for adjusting the stimulation voltage in response to the peak stimulation current signal. In one embodiment, the microcontroller 434 dynamically adjusts the stimulation voltage to keep the peak stimulation current signal at a constant value. In one embodiment, microcontroller 434 includes ADC 593 coupled to sample the peak stimulation current signal and drive the digital instruction to the DAC (via MOSI communication channel) to keep the peak stimulation current signal at the constant value.

The sinus treatment circuitry 500 of FIG. 5 provides a means to maintain a nearly constant (and comfortable) stimulation current in response to varying resistance or impedance. Turning to a more specific description of an embodiment of sinus treatment circuitry 500, a digital-to-analog converter (DAC) U6 receives commands from the microcontroller 434 to generate a square wave with a variable amplitude of 0 to +Vcc volts. The DAC output is current limited by R22 and is used to drive a push-pull output power stage comprised of Q5 and Q6, in the illustrated embodiment. The output of the push-pull stage is AC coupled by C10 and drives the primary side of a step-up transformer T1. C10 blocks the DC component of the square wave and allows through only the rising and falling edges of the square wave. The transformer converts the high current, low voltage edge input to the high voltage, low (microcurrent) stimulation current output, in the illustrated embodiment.

One end of the secondary side of the transformer is connected to the conductive tip. The other end of the secondary coil is connected to a dual diode array D7. The diode array acts as the stimulation current positive peak detector. R26 and C11 provide a simple sample and hold function of the detected peak. The peak detector output is buffered by op-amp U5. The output of the op-amp is then sampled by the ADC of the microcontroller.

During use, a control loop is formed by the DAC, peak detector, and the microcontroller ADC. The sensed positive peaks of the stimulation current are maintained at a constant level by controlling the DAC output. As the total resistance decreases, the control loop reduces the DAC output which reduces the amplitude of the edges being input to the transformer. The control loop effectively converts the voltage source output of the transformer to a constant current source, in the illustrated embodiment. In this manner, any uncomfortable surges in current are reduced during treatment.

Figure 6:
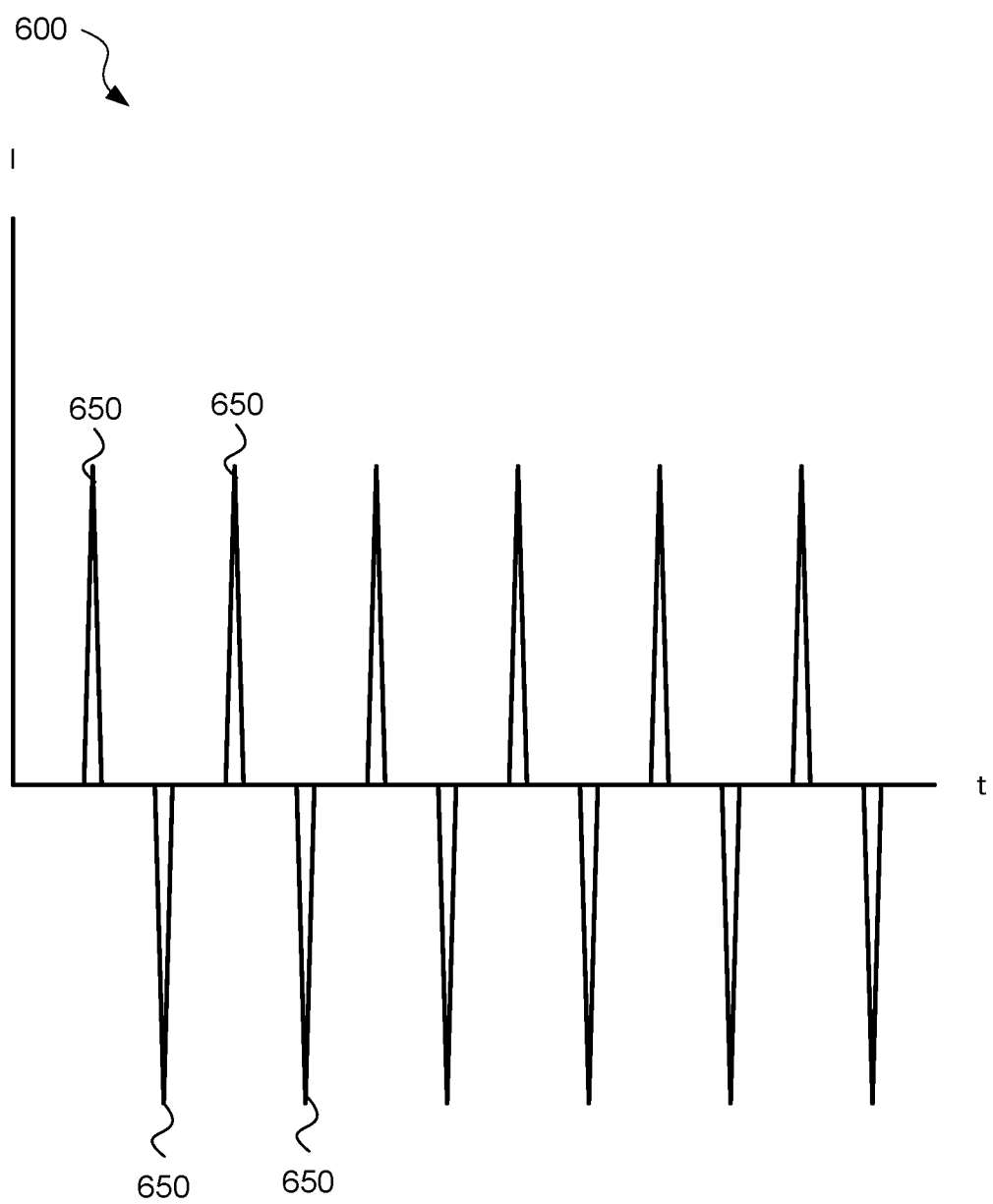
FIG. 6 is a graph of a treatment current vs time, according to an embodiment of the disclosure.

FIG. 6 is a graph of a treatment stimulation current (I) vs time (t), according to an embodiment. The treatment stimulation current is applied during a treatment mode of the handheld sinus treatment device 102 after the handheld sinus treatment device 112 has identified a treatment location. The treatment stimulation current provides relief to sinus discomfort and users.

According to an embodiment, the treatment stimulation current corresponds to a series of sharp current spikes 650 or peaks. According to an embodiment, successive current spikes alternate in direction such that every other current spike flows in a first direction, while intervening current spikes flow in a second, opposite, direction.

According to an embodiment, the current spikes 650 correspond to the rising and falling edges of a square wave voltage signal. In one embodiment, the treatment stimulation current is generated by feeding a square wave voltage signal to a transformer, such as the transformer T1, via a capacitor, such as the capacitor C10. Those of skill in the art will recognize, in light of the present disclosure, that a treatment stimulation current in accordance with FIG. 6 can be generated in various ways. All such other ways for generating the treatment stimulation current fall within the scope of the present disclosure.

In one embodiment, the treatment stimulation current has no DC offset. The lack of a DC offset can enhance the therapeutic effect of the treatment stimulation current. This is because, in one interpretation, the rapid changes in current magnitude and direction promote physiological effects that do not occur in the presence of a DC current.

In one embodiment, the sinus treatment circuitry 429, including the microcontroller 434 and the memory 432, adjust the stimulation voltage between the conductive tip and the return electrode to maintain a constant treatment stimulation current during the treatment mode. In one embodiment, maintaining a constant treatment stimulation current corresponds to causing the peaks of the treatment stimulation current to have substantially the same magnitudes. In one embodiment, maintaining a constant treatment stimulation current corresponds to causing the peaks of the treatment stimulation current to have substantially the same absolute values. Thus, the positive current peaks and the negative current peaks have the same absolute value, in one embodiment. Alternatively, maintaining a constant treatment stimulation current corresponds to causing the positive current peaks to have a same first magnitude, and causing the negative current peaks to have a same second magnitude.

In one embodiment, the peaks of the sinus treatment stimulation current have a magnitude less than or equal to 1000 μA. In one embodiment, the peaks of the treatment stimulation current have a magnitude less than or equal to 600 μA. In one embodiment, the sinus treatment stimulation current spikes 650 have an average current less than or equal to 1000 μA. In one embodiment, the sinus treatment stimulation current spikes 650 have an average current less than or equal to 600 μA.

In one embodiment, the frequency of the treatment stimulation current is less than 1000 Hz. In one embodiment, the period of a single treatment stimulation current cycle corresponds to the time between current peaks of the same direction. In one embodiment, the frequency of the treatment stimulation current is between 1 Hz and 100 Hz. In one embodiment, the spikes in the treatment stimulation current make up less than 10% of a single cycle. In one embodiment, the spikes in the treatment stimulation current make up less than 5% of a single cycle. In one embodiment, the spikes in the treatment stimulation current make up about 3% of a single cycle.

In one embodiment, during the treatment mode, the handheld sinus treatment device 102 measures the impedance by measuring the peaks of the treatment stimulation current. In one embodiment, the handheld sinus treatment device 102 adjusts a stimulation voltage applied between the conductive tip 108 and the return electrode 110 to bring the magnitude of the peaks of the treatment stimulation current back to a desired constant value.

In one embodiment, in the detection mode in which the handheld sinus treatment device identifies treatment locations, the handheld sinus treatment device 102 measures the impedance by applying a detection current with a waveform similar or identical to the treatment stimulation current waveform and measuring the magnitude of the current peaks of the detection current in order to determine the impedance. In one embodiment, the handheld sinus treatment device 102 measures the impedance by passing a detection current with a smaller magnitude than the treatment stimulation current. In one embodiment, during the detection mode, the handheld sinus treatment device 102 applies a detection voltage that is lower than the stimulation voltage applied during the treatment mode. In one embodiment, the handheld sinus treatment device measures the impedance by passing a detection current with a waveform entirely different than the treatment stimulation current waveform.

Those of skill in the art will recognize, in light of the present disclosure, that in practice the treatment current may vary from the graph 600. For example, the risetime and fall time of a given current spike may not be identical. The rise times and fall times of separate current spikes may not be identical to each other. A given current spike 650 can include, at the tail end, a brief portion that flows in the opposite direction to the primary direction of the current spike 650. In a constant current situation, current spikes may have slightly differing magnitudes while remaining substantially the same. There may be noise present among the current waveform. All such variations from the graph 600 fall within the scope of the present disclosure.

In one embodiment, the current spikes 650 are sharp increases in current followed by a sharp drop in current. In one embodiment, the rise time and fall time of a current spike 650 makes up 90% or more of the current spike 650.

FIG. 7 illustrates an example flow chart illustrating an example process 700 of operating a sinus treatment device, according to an embodiment of the disclosure.

In process block 702, an impedance is detected between a conductive tip (e.g., 108) of the handheld sinus treatment device (e.g., 102) and a return electrode (e.g., 110) of the handheld sinus treatment device (e.g., 102).

In process block 704, a treatment mode of the handheld sinus treatment device (e.g., 102) is initiated a stimulation voltage between the conductive tip (e.g., 108) and the return electrode (e.g., 110) when the impedance drops below a threshold.

In process block 706, a stimulation voltage is adjusted as the impedance between the conductive tip (e.g., 108) and the return electrode (e.g., 110) changes during the treatment mode.

In one embodiment, an initial stimulation voltage of the treatment mode driven across the conductive tip (e.g., 108) and the return electrode (e.g., 110) is a personal stimulation voltage saved to therapy profile in a memory of the handheld sinus treatment device (e.g., 102) and the personal stimulation voltage is based on a last stimulation voltage used by the handheld sinus treatment device (e.g., 102). In one embodiment, an initial stimulation voltage of the treatment mode driven across the conductive tip (e.g., 108) and the return electrode (e.g., 110) is a user selected stimulation voltage received from a user input of the handheld sinus treatment device (e.g., 102).

In one embodiment, process 500 further includes initiating a haptic feedback of the handheld sinus treatment device (e.g., 102) when the treatment mode is initiated.

In one embodiment, process 500 further includes illuminating a light emitting diode of the handheld sinus treatment device (e.g., 102) when the treatment mode is initiated.

In one embodiment, the return electrode (e.g., 110) is attached with a body (e.g., 106) of the handheld sinus treatment device (e.g., 102) that is formed to be held by a hand of a user of the handheld sinus treatment device (e.g., 102) and the return electrode (e.g., 110) is exposed to contact the hand of the user. In one embodiment, the return electrode (e.g., 110) is included in a body (e.g., 106) of the handheld sinus treatment device (e.g., 102), and wherein the body (e.g., 106) includes conductive polycarbonate to serve as the return electrode (e.g., 110).

In one embodiment, process 500 further includes turning off the handheld sinus treatment device (e.g., 102) when the impedance between the conductive tip (e.g., 108) and the return electrode (e.g., 110) is over a pre-determined threshold for a pre-determined time period (e.g., 2 minutes).

In one embodiment of process 500, driving the stimulation voltage across the conductive tip (e.g., 108) and the return electrode (e.g., 110) includes driving voltage pulses across the conductive tip (e.g., 108) and the return electrode (e.g., 110).

In one embodiment, the conductive tip (e.g., 108) is a spring-loaded tip to reduce the pressure of the conductive tip (e.g., 108) on a sinus skin area of the user of the handheld sinus treatment device (e.g., 102). In one embodiment, the conductive tip (e.g., 108) includes a conductor and a dielectric tip and both the conductor and the dielectric tip contact a sinus skin area of the user when the conductive tip (e.g., 108) is applied to the sinus skin area of the user. In one embodiment, the conductor includes carbon fiber.

In one embodiment, a method of operating a handheld sinus treatment device (e.g., 102) includes measuring a stimulation signal from a conductive tip (e.g., 108) of the handheld sinus treatment device (e.g., 102) where the stimulation signal is representative of a stimulation current between the conductive tip (e.g., 108) and a return electrode (e.g., 110) attached with a body (e.g., 106) of the handheld sinus treatment device (e.g., 102). The process further includes dynamically adjusting a stimulation voltage across the conductive tip (e.g., 108) and the return electrode (e.g., 110) to keep the stimulation current at a constant value in response to measuring the stimulation signal.

According to an embodiment, a method of operating a handheld sinus treatment device (e.g., 102) includes detecting an impedance between a conductive tip (e.g., 108) of the handheld sinus treatment device (e.g., 102) and a return electrode (e.g., 110) of the handheld sinus treatment device (e.g., 102). The method includes initiating a treatment mode of the handheld sinus treatment device (e.g., 102) when the impedance drops below a threshold by applying a stimulation voltage between the conductive tip (e.g., 108) and the return electrode (e.g., 110). The method includes changing the stimulation voltage as the impedance between the conductive tip (e.g., 108) and the return electrode (e.g., 110) changes during the treatment mode.

According to an embodiment, a method includes applying, with a handheld sinus treatment device (e.g., 102), sinus treatment stimulation to a sinus treatment location (e.g., 228) of a user by applying a stimulation current between a conductive tip (e.g., 108) and a return electrode (e.g., 110) of the handheld sinus treatment device (e.g., 102). The method includes measuring a stimulation signal representative of the stimulation current and maintaining a constant value of the stimulation current during treatment phase by dynamically adjusting a stimulation voltage between the conductive tip (e.g., 108) and the return electrode (e.g., 110) in response to measuring the stimulation signal.

According to an embodiment, a method of operating a handheld sinus treatment device (e.g., 102) includes initiating a treatment mode of the handheld sinus treatment device (e.g., 102) by applying a stimulation voltage between a conductive tip (e.g., 108) of a handheld sinus treatment device (e.g., 102) and a return electrode (e.g., 110) of the handheld sinus treatment device (e.g., 102). The method includes changing the stimulation voltage as an impedance between the conductive tip (e.g., 108) and the return electrode (e.g., 110) changes during the treatment mode.

According to an embodiment, a handheld sinus treatment device (e.g., 102) includes a conductive tip (e.g., 108), a return electrode (e.g., 110) operatively coupled to a body (e.g., 106) of the handheld sinus treatment device (e.g., 102), and a stimulation driver stage coupled to apply a stimulation voltage between the conductive tip (e.g., 108) and the return electrode (e.g., 110). The handheld sinus treatment device (e.g., 102) includes a peak detector coupled to generate a peak stimulation current signal in response to receiving a stimulation signal from the conductive tip (e.g., 108). The handheld sinus treatment device (e.g., 102) includes a microcontroller (e.g., 434) coupled to receive the peak stimulation current signal from the peak detector and coupled to the stimulation driver stage for adjusting the stimulation voltage in response to the peak stimulation current signal. The microcontroller (e.g., 434) dynamically adjusts the stimulation voltage to keep the peak stimulation current signal at a constant value.

According to an embodiment, a handheld sinus treatment device (e.g., 102) includes a housing (e.g., 106) configured to be held in a hand of user, a conductive tip (e.g., 108) coupled to the housing (e.g., 106), and a return electrode (e.g., 110) positioned on the housing (e.g., 110) such that when a user holds the housing (e.g., 106) the hand of the user is in contact with the return electrode (e.g., 110). The handheld sinus treatment device (e.g., 102) includes sinus treatment circuitry positioned within the housing (e.g., 106) and configured to detect an impedance between the conductive tip (e.g., 108) and the return electrode (e.g., 110) and to enter a treatment mode responsive to the impedance dropping below a threshold by applying a stimulation current between the conductive tip (e.g., 108) and the return electrode (e.g., 110).

According to an embodiment, a method includes detecting, during a detection mode, an impedance between a conductive tip of a sinus treatment device and a return electrode of the sinus treatment device. The method includes initiating a treatment mode of the sinus treatment device when the impedance drops below a threshold including passing a treatment stimulation current between the conductive tip and the return electrode. The treatment stimulation current includes a series of current spikes.

According to an embodiment, a method includes detecting, during a detection mode, an impedance between a conductive tip of the sinus treatment device and a return electrode of the sinus treatment device. The method includes initiating a treatment mode of the sinus treatment device when the impedance drops below a threshold including passing a treatment stimulation current between the conductive tip and the return electrode. The treatment stimulation current has a magnitude less than 1000 µA.

According to an embodiment, a method includes initiating a treatment mode of a sinus treatment device and passing, during the treatment mode of the sinus treatment device, a treatment stimulation current between a conductive tip of the sinus treatment device and the return electrode of the sinus treatment device. The treatment stimulation current has a magnitude less than 1000 µA.

According to an embodiment, a method includes initiating a treatment mode of a sinus treatment device; and passing, during the treatment mode of the sinus treatment device, a treatment stimulation current between a conductive tip of the sinus treatment device and the return electrode of the sinus treatment device, wherein the treatment stimulation current includes a series of current spikes with a frequency less than 1000 Hz and a magnitude less than 1000 µA.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible non-transitory machine-readable storage medium includes any mechanism that provides (i.e., stores) information in a form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A method, comprising:
   applying, with a sinus treatment device, sinus treatment stimulation to a sinus treatment location of a user by applying a stimulation current including a series of current spikes between a conductive tip and a return electrode of the sinus treatment device;
   measuring a stimulation signal representative of the stimulation current; and
   maintaining a constant magnitude of the series of current spikes during a treatment mode by dynamically adjusting a stimulation voltage between the conductive tip and the return electrode in response to measuring the stimulation signal;
   wherein an initial stimulation voltage of the treatment mode applied between the conductive tip and the return electrode is a personal stimulation voltage saved to a therapy profile in a memory of the sinus treatment device, and wherein the personal stimulation voltage is based on a most recent stimulation voltage used by the sinus treatment device.

2. The method of claim 1, further comprising:
   detecting, during a detection mode of the sinus treatment device, an impedance between the conductive tip and the return electrode; and
   entering the treatment mode by applying the stimulation current responsive to the impedance dropping below a threshold, wherein the treatment mode includes applying the stimulation voltage between the conductive tip and the return electrode.

3. The method of claim 1, wherein the series of current spikes include current spikes of alternating direction, and wherein maintaining the constant magnitude of the series of current spikes includes maintaining a constant absolute value of the magnitude of the series of current spikes of alternating direction.

4. The method of claim 1, wherein an initial stimulation voltage of the treatment mode applied between the conductive tip and the return electrode is a user selected stimulation voltage received from a user input of the sinus treatment device.

5. The method of claim 1, further comprising initiating a haptic feedback of the sinus treatment device when the treatment mode is initiated.

6. The method of claim 1, wherein the return electrode is attached to a body of the sinus treatment device that is formed to be held by a hand of the user of the sinus treatment device, and wherein the return electrode is exposed to contact the hand of the user.

7. The method of claim 1, wherein the return electrode includes a conductive body of the sinus treatment device.

8. The method of claim 1, wherein applying the stimulation voltage between the conductive tip and the return electrode includes driving voltage pulses across the conductive tip and the return electrode.

9. The method of claim 1, wherein the stimulation current has a frequency less than 1000 Hz.

10. The method of claim 9, wherein the stimulation current has a frequency between 1 Hz and 100 Hz.

11. The method of claim 1, wherein the stimulation current has a magnitude less than 1000 µA.

12. The method of claim 1, wherein the stimulation voltage has a DC component of 0 V.

13. The method of claim 1, further comprising:
measuring an impedance between the conductive tip and the return electrode during the treatment mode; and
maintaining the constant magnitude of the current spikes during the treatment mode by adjusting the stimulation voltage responsive to changes in the impedance during the treatment mode.

* * * * *